(12) United States Patent
Ogawa

(10) Patent No.: US 6,914,623 B2
(45) Date of Patent: Jul. 5, 2005

(54) IMAGE PROCESSING MEASURING APPARATUS AND MEASURING ENDOSCOPE APPARATUS

(75) Inventor: Kiyotomi Ogawa, Tokyo (JP)

(73) Assignee: Olympus Corporation (JP)

( * ) Notice: Subject to any disclaimer, the term of this patent is extended or adjusted under 35 U.S.C. 154(b) by 589 days.

(21) Appl. No.: 10/158,417

(22) Filed: May 29, 2002

(65) Prior Publication Data

US 2002/0191074 A1 Dec. 19, 2002

(30) Foreign Application Priority Data

May 30, 2001 (JP) ........................................ 2001-162868

(51) Int. Cl.$^7$ .............................. H04N 7/18; A61B 1/04
(52) U.S. Cl. ............................ 348/45; 348/65; 600/111
(58) Field of Search .............................. 348/45, 51, 65; 600/101, 109, 111–112

(56) References Cited

U.S. PATENT DOCUMENTS 4,898,450 A * 2/1990 Jannson et al. ............... 385/50
5,469,254 A * 11/1995 Konomura ............... 356/241.1

FOREIGN PATENT DOCUMENTS

JP 2001-75019 3/2001
JP 2001-167272 6/2001

* cited by examiner

Primary Examiner—Vu Le
(74) Attorney, Agent, or Firm—Ostrolenk, Faber, Gerb & Soffen, LLP

(57) ABSTRACT

A processing unit includes an estimating unit for estimating three-dimensional coordinates at an arbitrary point on an observation image and obtaining the estimation result and the reliability of the estimation result. A concave and convex datum line setting unit estimates the reliability of a point on the cut-off datum line or on an extending line of the cut-off datum line based on the reliability of the estimation result of the estimating unit, extracts only a point whose reliability is high and setting both new ends, and sets a concave and convex datum line as a predetermined datum based on both the new ends. The concave and convex datum line setting unit sets a concave and convex datum line as a predetermined datum for processing the cross-section information to create concave and convex information indicating a relative concave and convex state with respect to the predetermined datum based on both the set new ends. Accordingly, the reliability of the concave and convex datum line as the datum of the concave and convex information is improved and more accurate information on the concave and convex state of a target can be presented to a user.

30 Claims, 14 Drawing Sheets

US 6,914,623 B2

IMAGE PROCESSING MEASURING APPARATUS AND MEASURING ENDOSCOPE APPARATUS

This application claims benefit of Japanese Application No. 2001-162868 filed on May 30, 2001, the contents of which are incorporated by this reference.

BACKGROUND OF THE INVENTION

1. Field of the Invention

The present invention relates to an image-processing measuring apparatus and a measuring endoscope apparatus for measuring a position of a measuring target point by using an image obtained from one or plurality of view points and, more particularly, to an image-processing measuring apparatus and a measuring endoscope apparatus for objectively recognizing a concave and convex portion of a target by obtaining and displaying contour information of the target.

2. Description of the Related Art

In general, the detailed examination of a subject using an endoscope requires the measurement of the position of the subject. To satisfy this requirement, conventionally, various measuring apparatuses using the endoscope are proposed.

For example, Japanese Unexamined Patent Application Publication No. 2001-75019 discloses a measuring endoscope apparatus for generating contour information by stereo measurement and displaying it as a contour line. Further, Japanese Unexamined Patent Application Publication No. 2001-167272 by the applicant of the present invention discloses a subject measuring display apparatus which generates corresponding information between a contour line and an image pick-up signal and displaying it.

In the above-mentioned related arts, information on the contour of a cross section on a cut-off plane on which an observation target exists is generated for purpose of, mainly, obtaining objective information on a concave and convex state of the target, namely, concave and convex information.

In stereo measurement for obtaining a position at a measuring target point based on the principle of triangulation by using a plurality of images from a plurality of view points, it is necessary that, at a measuring target point inputted by a user on one screen, the measuring target points on the plurality of images corresponding to the view points made correspondent. However, there is a possibility that the correspondence of the target points fails due to occlusion or halation depending on a user's input.

However, in a contour information generating unit, a cut-off datum line as a datum for determining the cut-off plane also functions as a concave and convex datum line as a datum of the concave and convex information. Therefore, at two points (measuring target points) inputted by the user upon designating the cut-off datum line, if the correspondence of any of the two points fails, there is a possibility that obtained contour information becomes inaccurate.

SUMMARY OF THE INVENTION

It is an object of the present invention to provide an image-processing measuring apparatus and a measuring endoscope apparatus, by which more accurate information on a concave and convex state of a target can be presented to a user by improving the reliability of a concave and convex datum line as a datum of the concave and convex information.

According to the present invention, there is provided an image-processing measuring apparatus comprising: one or a plurality of image pick-up units for observation; one or a plurality of observation optical systems for forming an observation target on the image pick-up unit as an observation image from one or a plurality of view points; a processing unit for receiving a signal from the image pick-up unit, performing processing of the received signal, and generating a video signal; a display device for receiving and displaying the video signal from the processing unit and displaying the observed image; an estimating unit for estimating three-dimensional coordinates at an arbitrary point on the observed image based on an image signal in each view point obtained by the image pick-up unit, and obtaining the estimation result and the reliability of the estimation result; a cut-off datum line input unit for inputting a cut-off datum line as a datum for setting a position of a cut-off plane of the observation target; a cross-section information generating unit for generating cross-section information of the observed target on the cut-off plane based on the estimation result of the estimating unit; a concave and convex datum line setting unit for estimating the reliability of a point on the cut-off datum line or on an extending line of the cut-off datum line based on the reliability of the estimation result of the estimating unit, extracting only a point whose reliability is high and setting both new ends, and setting a concave and convex datum line as a predetermined datum based on both the new ends; a concave and convex information generating unit for generating concave and convex information by processing the cross-section information to generate the concave and convex information indicating a relative concave and convex state with respect to the concave and convex datum line; a concave and convex information processing unit for processing the concave and convex information to a visualized concave and convex index; and a concave and convex index display unit for displaying the concave and convex index.

According to the present invention, there is provided a measuring endoscope apparatus comprising: an endoscope insertion portion having at a tip thereof, one or a plurality of image pick-up units for observation and one or a plurality of observation optical systems for forming an observation target on the image pick-up unit as an observation image in one or a plurality of view points; a processing unit for receiving a signal from the image pick-up unit, performing processing of the received signal, and generating a video signal; a display device for receiving and displaying the video signal from the processing unit and displaying the observation image; an estimating unit for estimating three-dimensional coordinates at an arbitrary point on the observed image based on an image signal in each view point obtained by the image pick-up unit, and obtaining the estimation result and the reliability of the estimation result; a cut-off datum line input unit for inputting a cut-off datum line as a datum for setting a position of a cut-off plane of the observation target; a cross-section information generating unit for generating cross-section information of the observation target on the cut-off plane based on the estimation result of the estimating unit; a concave and convex datum line setting unit for estimating the reliability of a point on the cut-off datum line or on an extending line of the cut-off datum line based on the reliability of the estimation result of the estimating unit, extracting only a point whose reliability is high and setting both new ends, and setting a concave and convex datum line as a predetermined datum based on both the new ends; a concave and convex information generating unit for generating concave and convex information by processing the cross-section information to the concave and convex information indicating a concave and convex state relative to the concave and convex datum line; a concave and convex information processing unit for processing the concave and convex information to create a visualized concave and convex index; and a concave and convex index display unit for displaying the concave and convex index.

Further, according to the present invention, there is provided an image-processing measuring apparatus comprising: one or a plurality of image pick-up units for observation; one or a plurality of observation optical systems for forming an observation target on the image pick-up unit as an observation image from one or a plurality of view points; a processing unit for receiving a signal from the image pick-up unit, performing processing of the received signal, and generating a video signal; and a display device for receiving and displaying the video signal from the processing unit and displaying the observed image, wherein the processing unit comprises an estimating unit for estimating three-dimensional coordinates at an arbitrary point on the observation image based on an image signal in each view point obtained by the image pick-up unit, and obtaining the estimation result and the reliability of the estimation result. The image-processing measuring apparatus further comprises: a cut-off datum line input unit for inputting a cut-off datum line as a datum for setting a position of a cut-off plane of the observation target; a cross-section information generating unit for generating cross-section information of the observation target on the cut-off plane based on the estimation result of the estimating unit; a concave and convex datum line setting unit for estimating the reliability of a point on the cut-off datum line or on an extending line of the cut-off datum line based on the reliability of the estimation result of the estimating unit, extracting only a point whose reliability is high and setting both new ends, and setting a concave and convex datum line as a predetermined datum indicating a relative concave and convex state with respect to the predetermined datum based on both the new ends; a concave and convex information generating unit for generating the concave and convex information based on the cross-section information and the concave and convex datum line; a concave and convex information processing unit for processing the concave and convex information to create a concave and convex index by which the concave and convex information is visualized; and a concave and convex index display unit for displaying the concave and convex index.

Furthermore, there is provided a measuring endoscope apparatus comprising: a long insertion portion having at a tip thereof, one or a plurality of image pick-up units for observation and one or a plurality of observation optical systems for forming an observation target on the image pick-up unit as an observed image in one or a plurality of view points; a processing unit for receiving a signal from the image pick-up unit, performing processing of the received signal, and generating a video signal; and a display device for receiving and displaying the video signal from the processing unit and displaying the observed image, wherein the processing unit comprises an estimating unit for estimating three-dimensional coordinates at an arbitrary point on the observed image based on an image signal in each view point obtained by the image pick-up unit, and obtaining the estimation result and the reliability of the estimation result. The measuring endoscope apparatus further comprises: a cut-off datum line input unit for inputting a cut-off datum line as a datum for setting a position of a cut-off plane for cross-section information of the observation target; a cross-section information generating unit for generating the cross-section information of the observation target on the cut-off plane based on the estimation result of the estimating unit; a concave and convex datum line setting unit for estimating the reliability of a point on the cut-off datum line or on an extending line of the cut-off datum line based on the reliability of the estimation result of the estimating unit, extracting only a point whose reliability is high and setting both new ends, and setting a concave and convex datum line as a predetermined datum for processing the cross-section information to create concave and convex information indicating a relative concave and convex state with respect to the predetermined datum based on both the new ends; a concave and convex information generating unit for generating the concave and convex information based on the cross-section information and the concave and convex datum line; a concave and convex information processing unit for processing the concave and convex information to create a concave and convex index by which the concave and convex information is visualized; and a concave and convex index display unit for displaying the concave and convex index.

The above and other objects, features and advantages of the invention will become more clearly understood from the following description referring to the accompanying drawings.

DESCRIPTION OF THE PREFERRED EMBODIMENTS

Hereinbelow, embodiments of the present invention will be described with reference to the drawings.

(First Embodiment)

Figure 1:
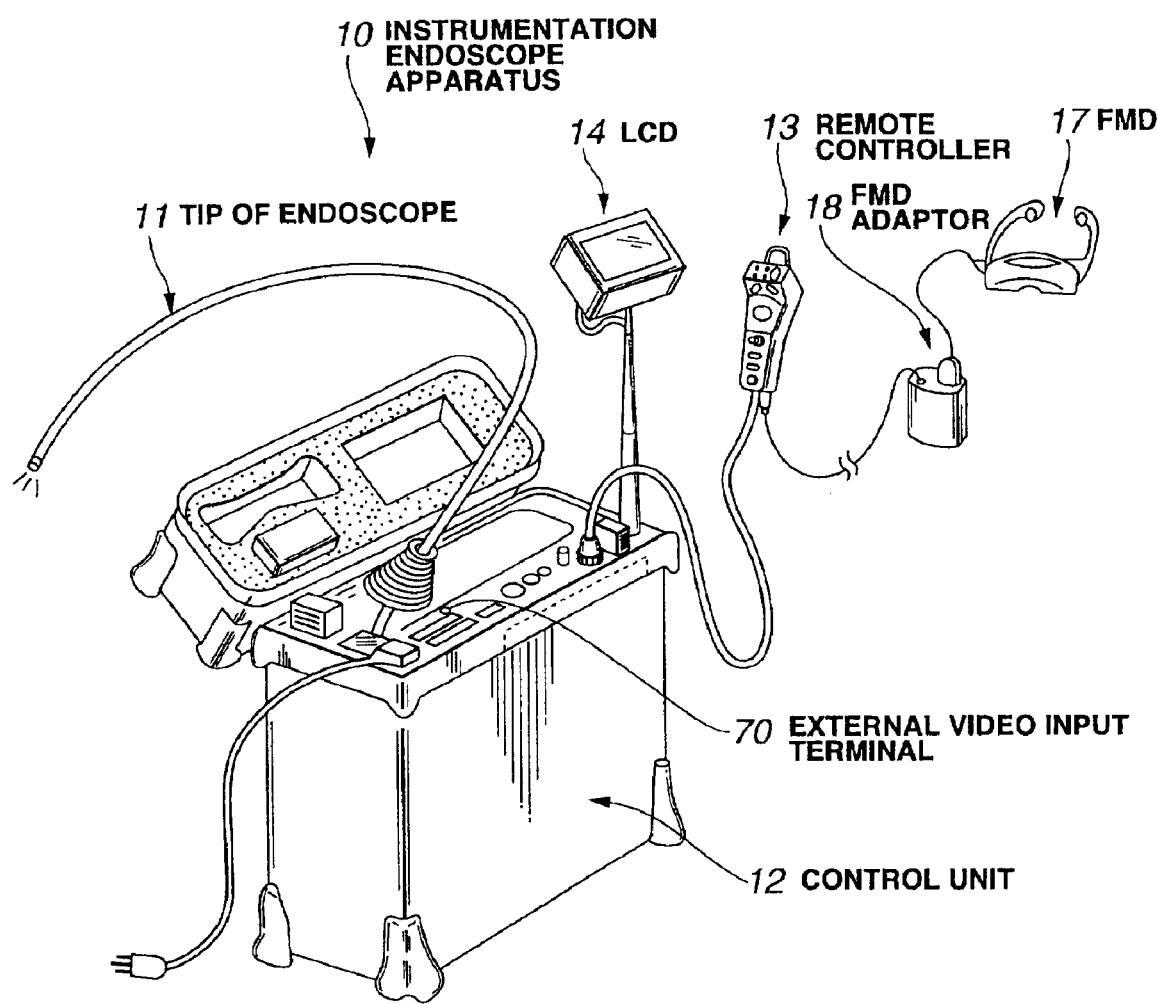
FIG. 1 is a diagram schematically showing the structure of a measuring endoscope apparatus according to a first embodiment of the present invention.
Figure 2:
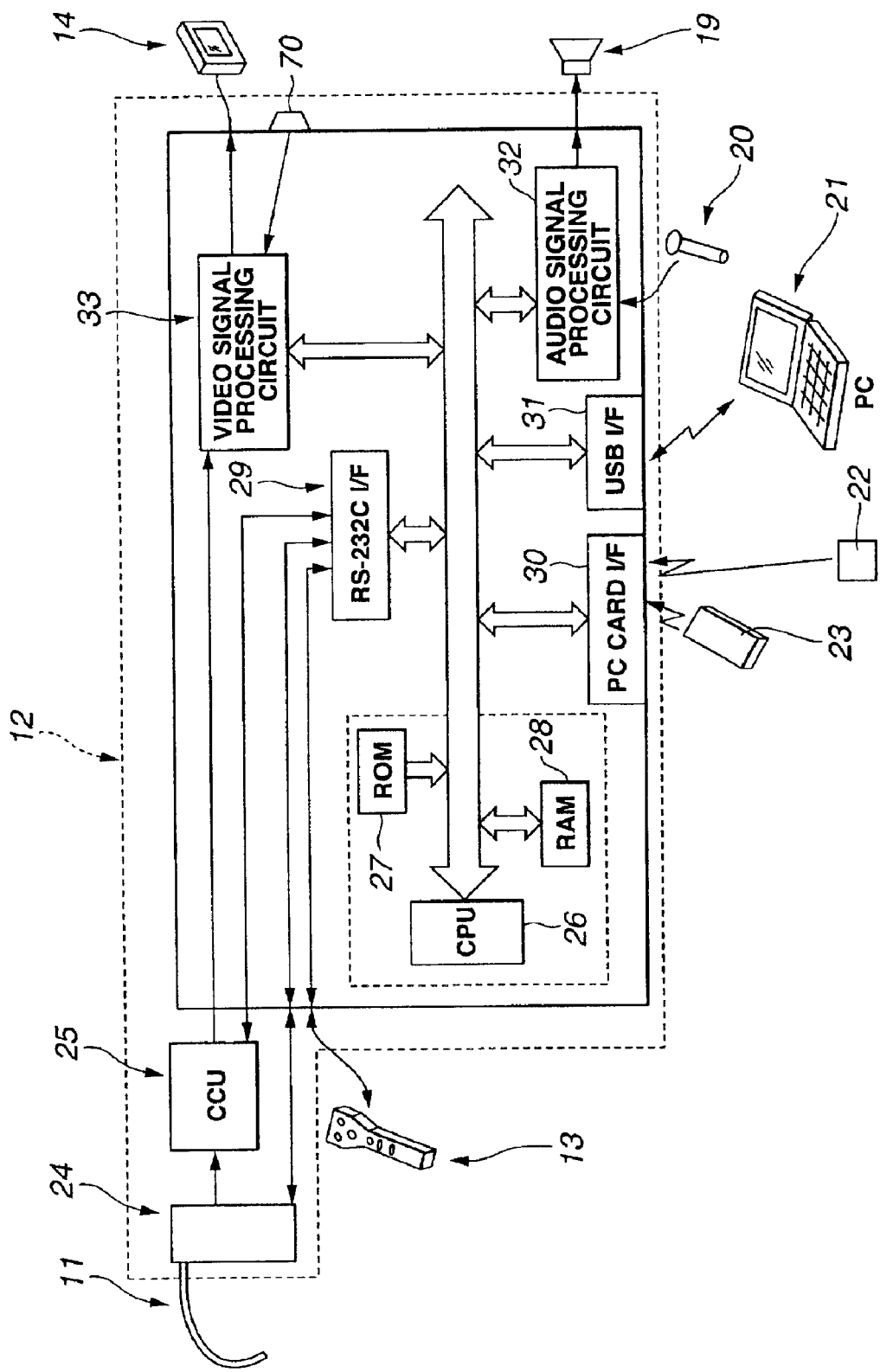
FIG. 2 is a block diagram showing the structure of circuitries in the measuring endoscope apparatus in FIG. 1.
Figure 3:
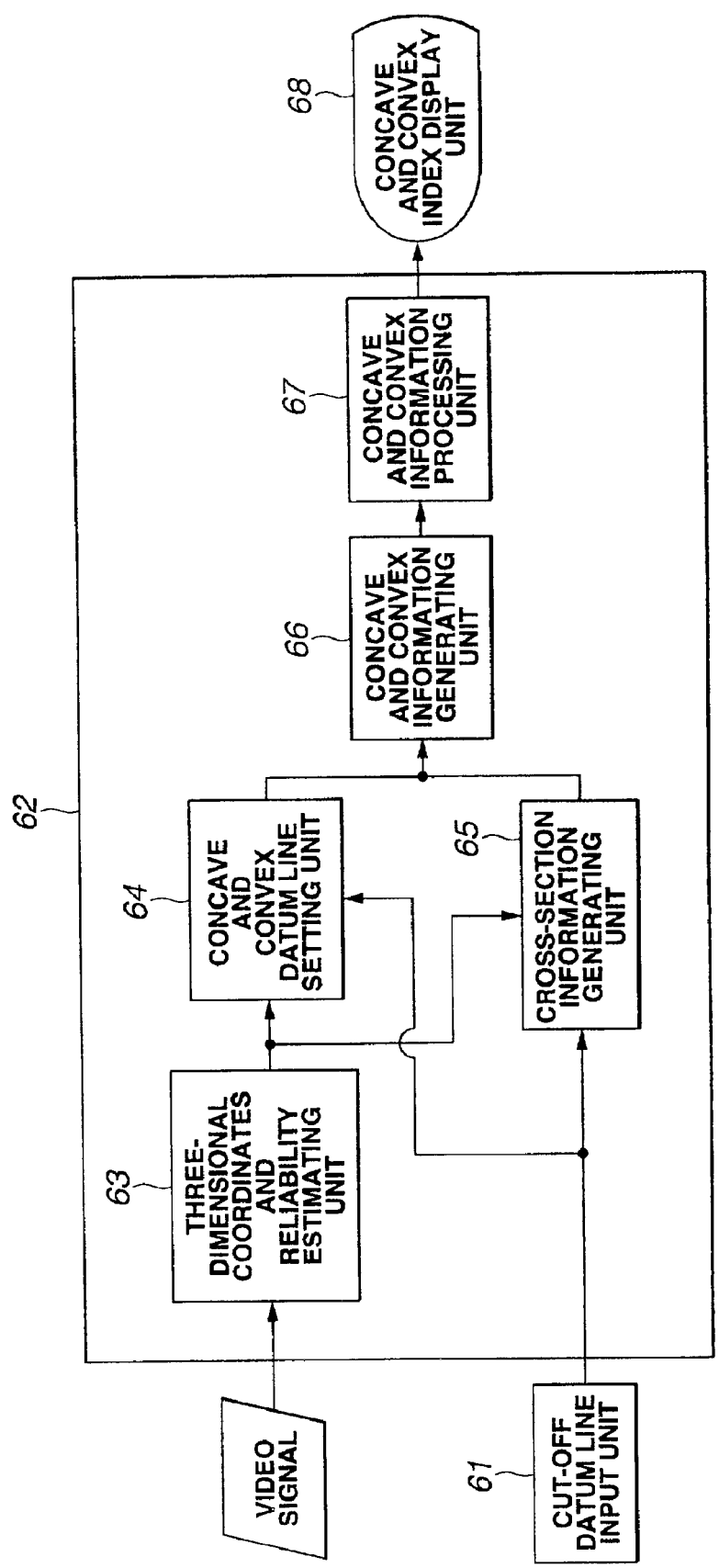
FIG. 3 is a functional block diagram showing the processing of a CPU in FIG. 2.
Figure 4:
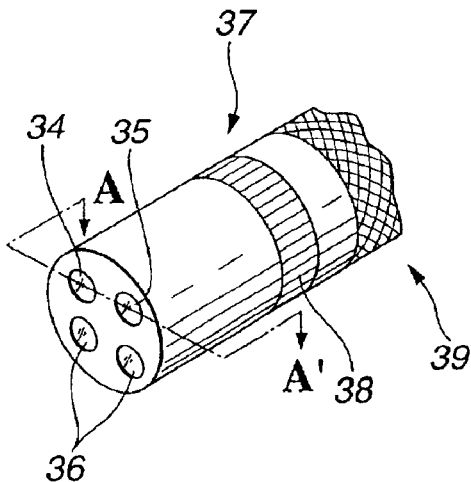
FIG. 4 is a perspective view showing the structure of a tip of an endoscope, to which a stereo optical adaptor of the measuring endoscope apparatus is attached.
Figure 5:
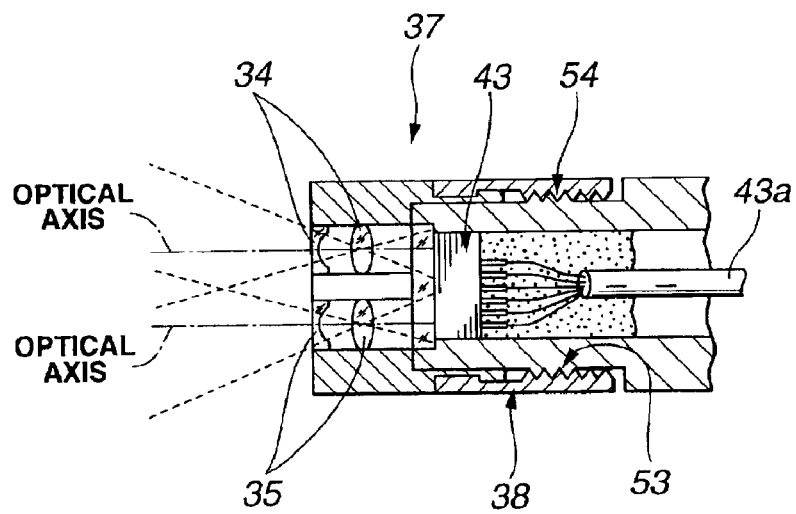
FIG. 5 is a sectional view of an A—A cut-plane in FIG. 4.
Figure 6:
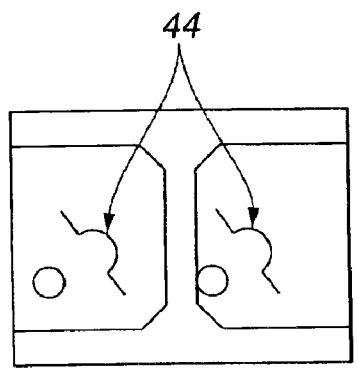
FIG. 6 is an explanatory diagram showing an endoscope image in a state in which the stereo optical adaptor in FIG. 4 is attached.
Figure 7:
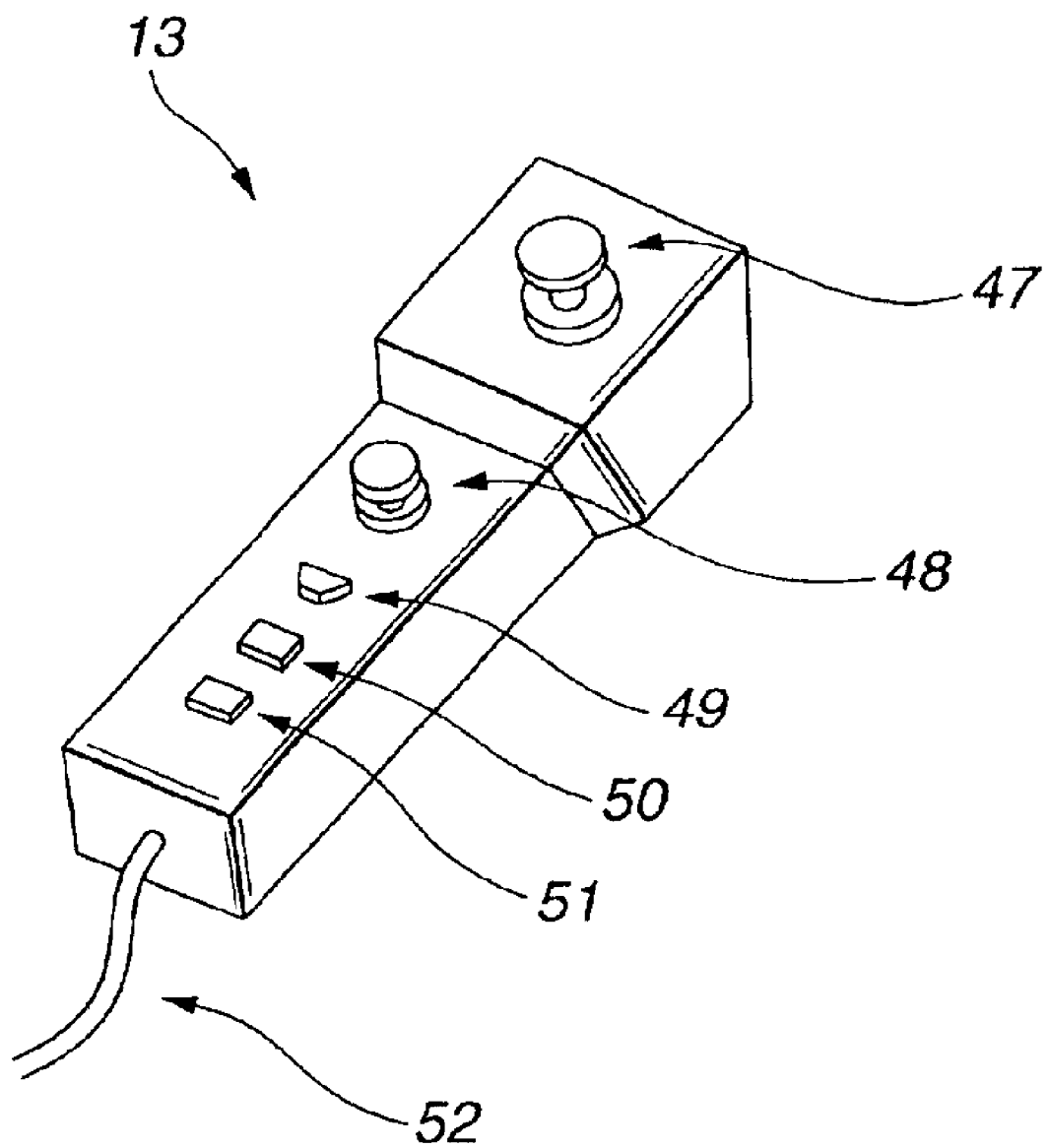
FIG. 7 is a perspective view showing the structure of a remote controller in FIG. 1.
Figure 8:
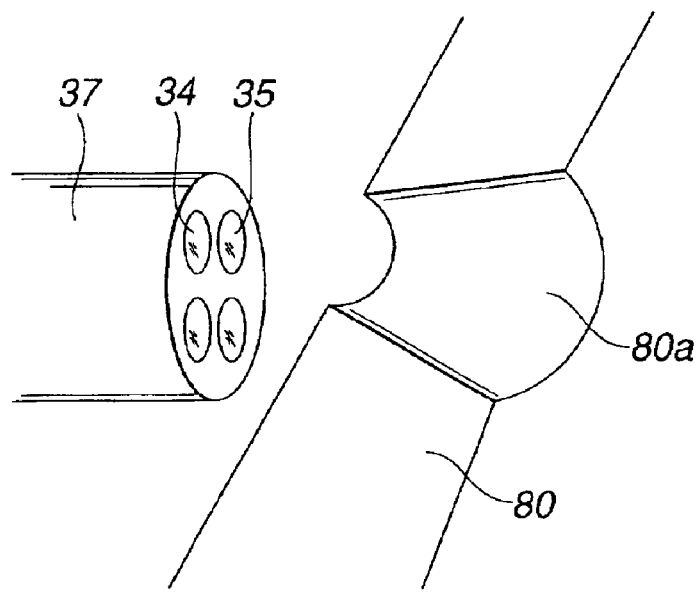
FIG. 8 is an explanatory diagram showing a state in which a concave portion is observed by the tip of the endoscope in FIG. 4.
Figure 9:
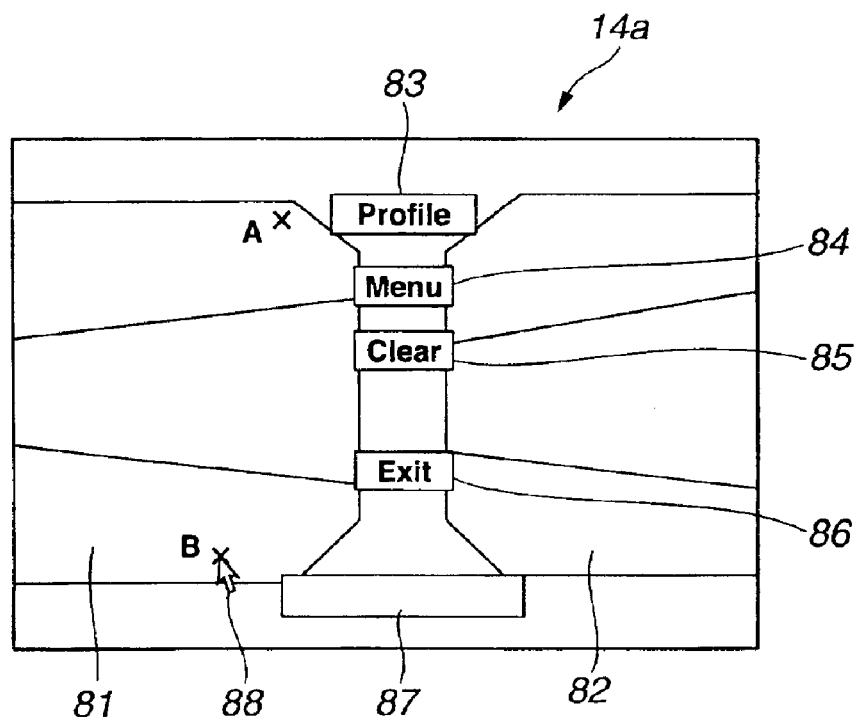
FIG. 9 is an explanatory diagram showing a screen for executing a stereo measurement by the measuring endoscope apparatus in FIG. 1.
Figure 10:
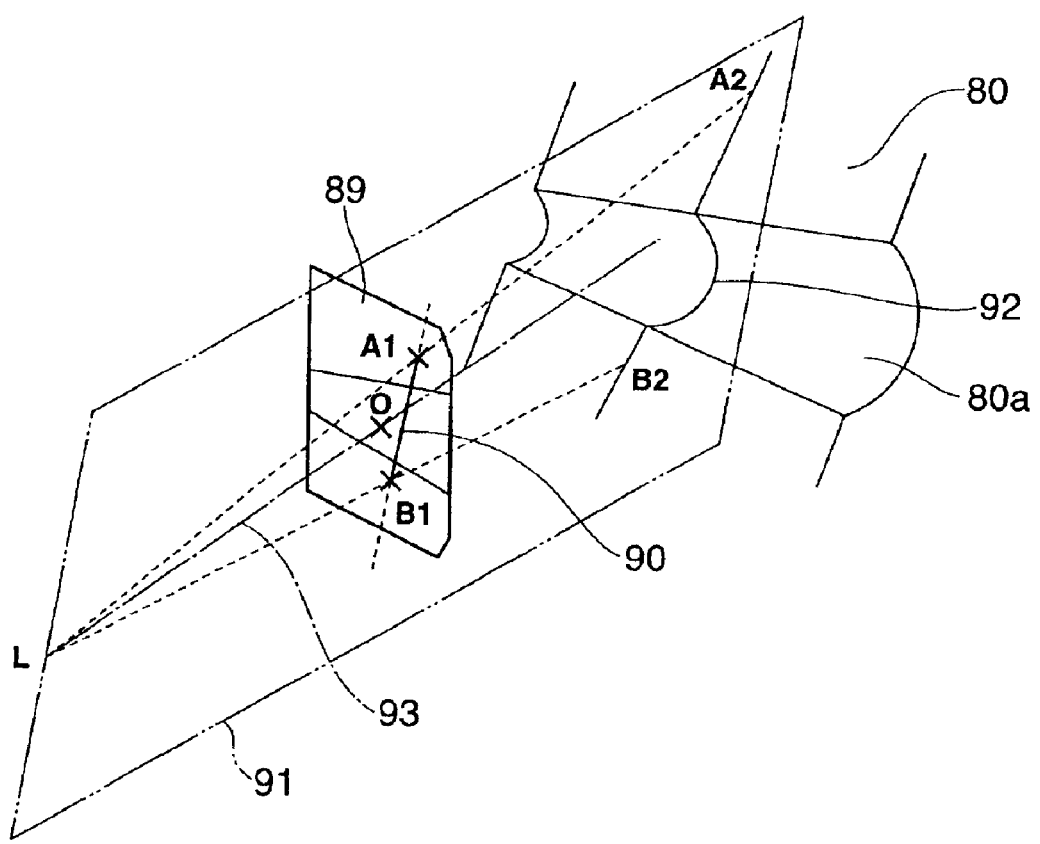
FIG. 10 is an explanatory diagram showing a cut-off plane and a cross-sectional outer line which are determined by operating the remote controller in FIG. 1.
Figure 11:
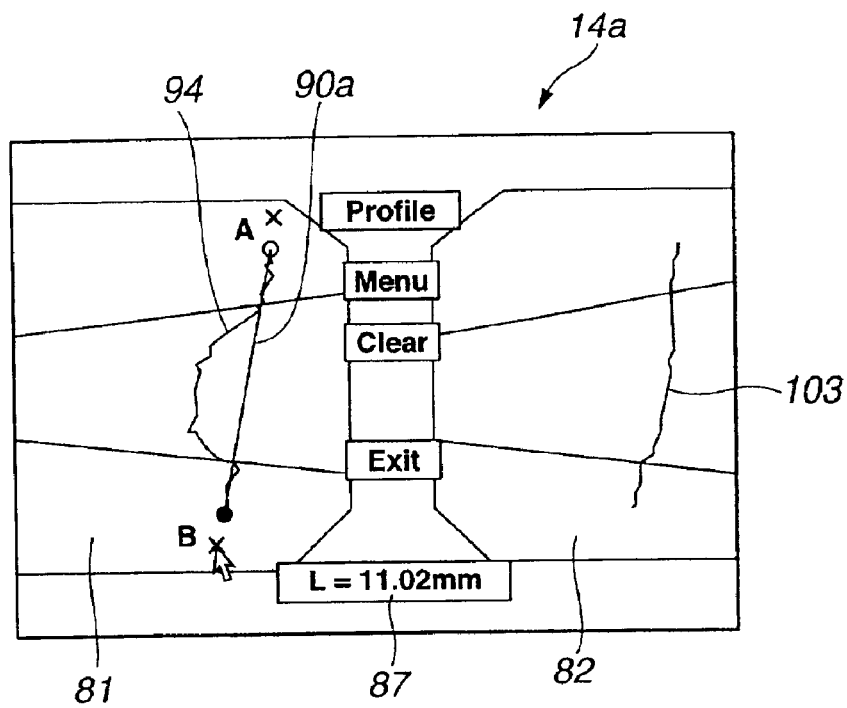
FIG. 11 is an explanatory diagram showing a first example of a screen on which a concave and convex index is displayed by the measuring endoscope apparatus in FIG. 1.
Figure 12:
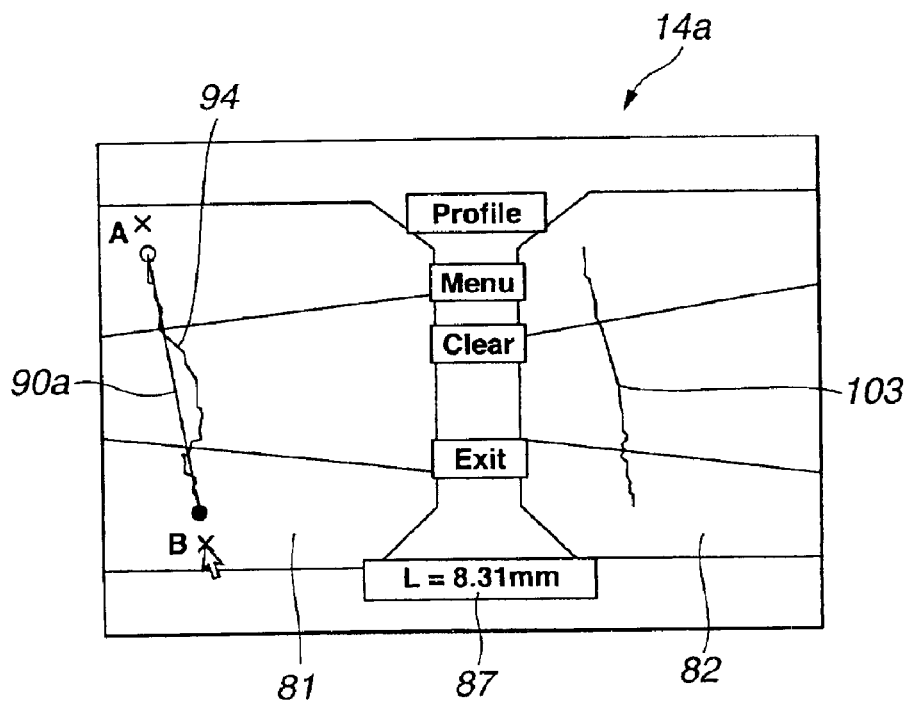
FIG. 12 is an explanatory diagram showing a second example of the screen on which the concave and convex index is displayed by the measuring endoscope apparatus in FIG. 1.
Figure 13:
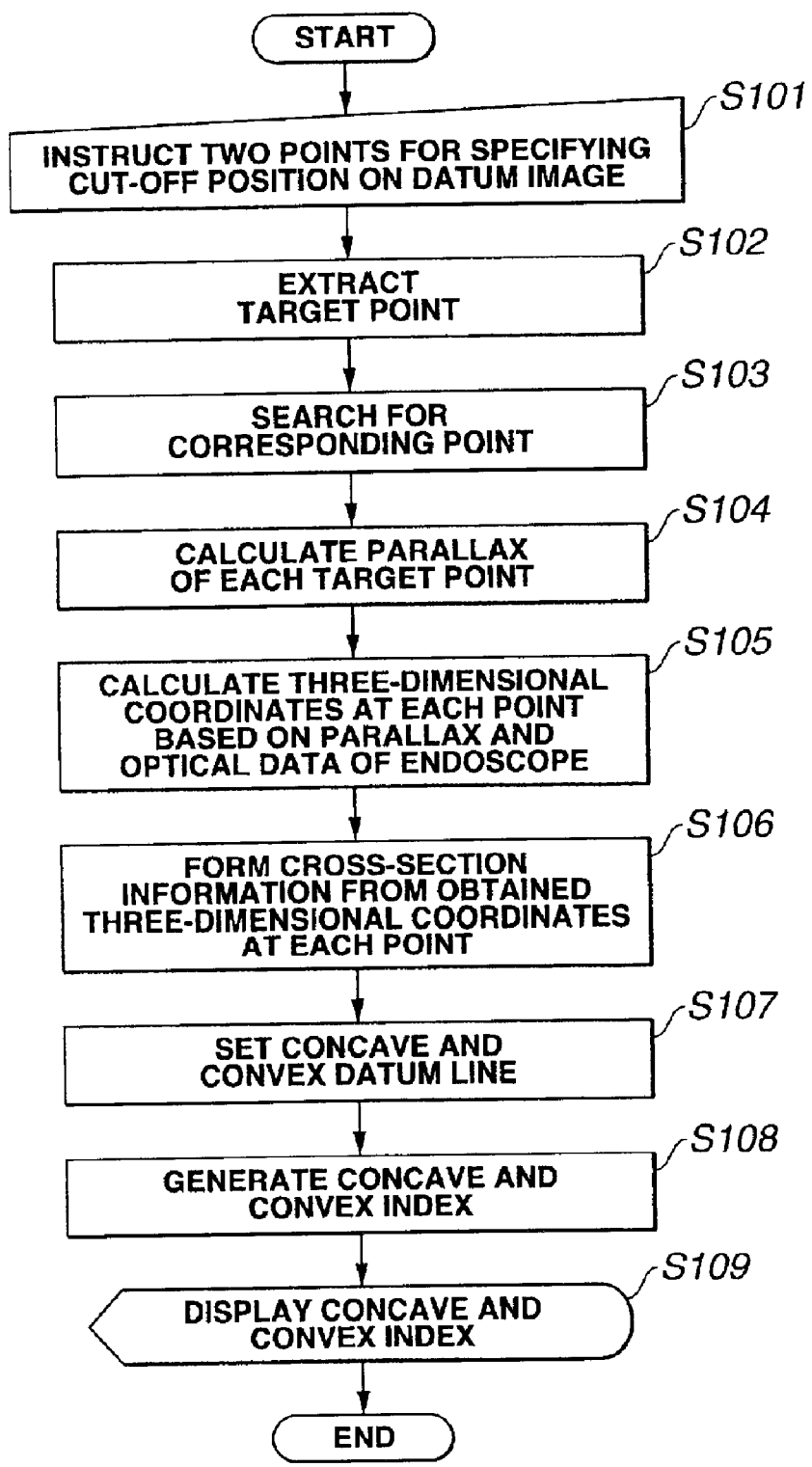
FIG. 13 is a flowchart showing processing for measuring a cross section by the measuring endoscope apparatus in FIG. 1.
Figure 14:
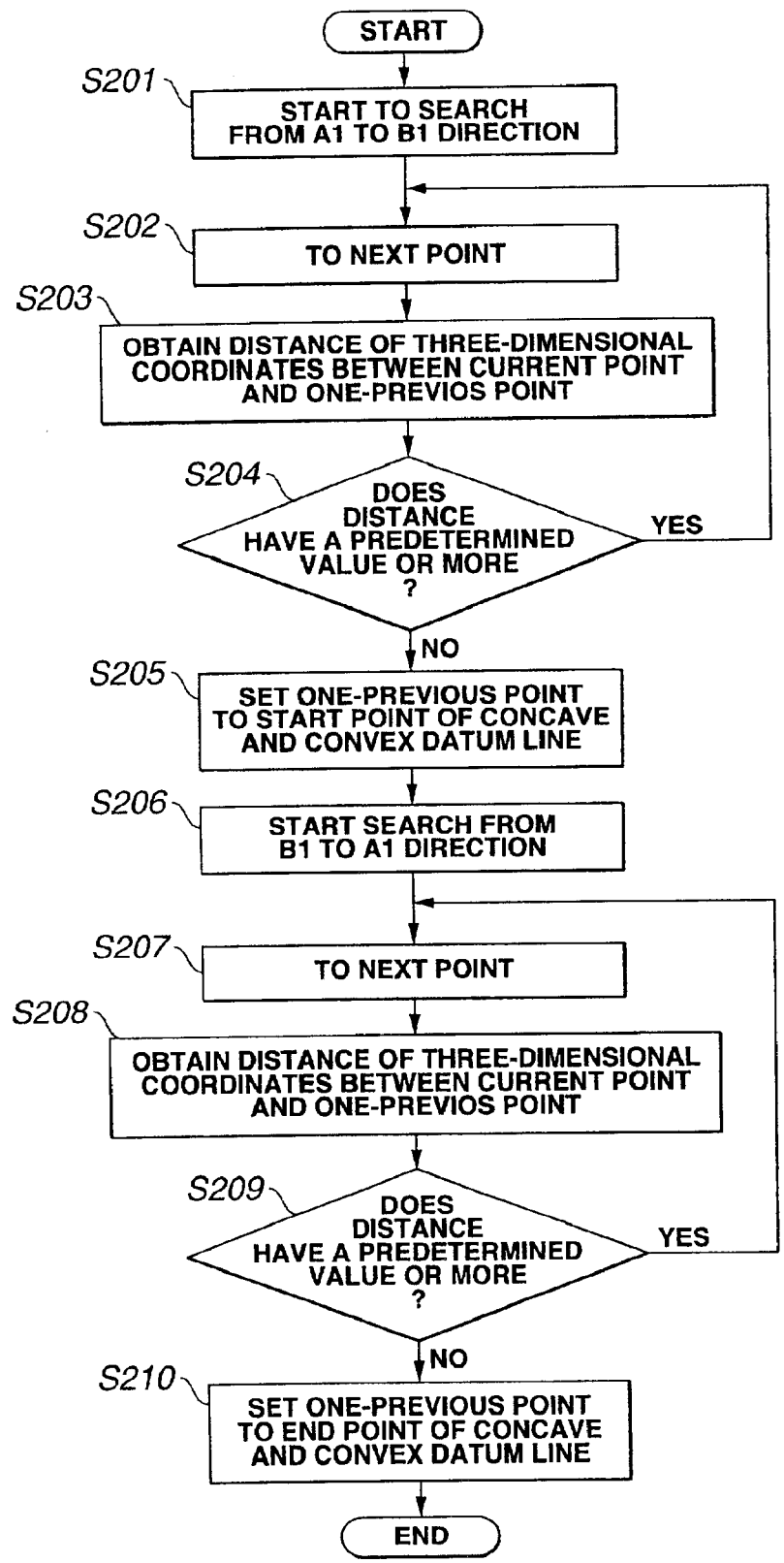
FIG. 14 is a flowchart for explaining in detail content of S107 in FIG. 13.

FIGS. 1 to 14 relate to a first embodiment of the present invention. FIG. 1 is a perspective view showing the system structure of the measuring endoscope apparatus, FIG. 2 is a block diagram showing the structure of circuitries in the measuring endoscope apparatus in FIG. 1, FIG. 3 is a functional block diagram showing processing of a CPU in FIG. 2, FIG. 4 is a perspective view showing the structure of a tip of an endoscope, to which a stereo optical adaptor is attached, FIG. 5 is a sectional view showing an A—A cut-plane in FIG. 4, FIG. 6 is an explanatory diagram showing an endoscope image in a state in which the stereo optical adaptor is attached, FIG. 7 is a perspective view showing the structure of a remote controller, FIG. 8 is an explanatory diagram showing a state in which a concave portion is observed by the tip of the endoscope, FIG. 9 is an explanatory diagram showing a screen for executing stereo measurement, FIG. 10 is an explanatory diagram showing a cut-off plane and a cross-sectional outer line which are determined by operating the remote controller, FIG. 11 is an explanatory diagram showing a first example of a screen on which a concave and convex index is displayed, FIG. 12 is an explanatory diagram showing a second example of the screen on which the concave and convex index is displayed, FIG. 13 is a flowchart showing processing for measuring of a cross section by the measuring endoscope apparatus, and FIG. 14 is a flowchart for explaining in detail content of S107 in FIG. 13.

First, the system structure of a measuring endoscope apparatus 10 will be described according to the first embodiment with reference to FIG. 1.

Referring to FIG. 1, the measuring endoscope apparatus 10 comprises an endoscope insertion portion 11 to which at least two types of optical adaptors for stereo measurement and normal measurement can detachably be attached, a control unit 12 for accommodating the endoscope insertion potion 11, a remote controller 13 for performing operation necessary for executing various control operations of the entire system of the measuring endoscope apparatus 10, a liquid crystal monitor (hereinafter, referred to as an LCD) for displaying an endoscope image and content of the operation control (e.g., a processing menu) 14, a face mounted display (hereinafter, referred to as an FMD) 17, on which a normal endoscope image can be viewed or a pseudo stereo image of the endoscope image can be stereoscopically be viewed, and an FMD adaptor 18 for supplying image data to the FMD 17.

Next, the system structure of the measuring endoscope apparatus 10 will be described in detail with reference to FIG. 2.

Referring to FIG. 2, the endoscope insertion portion 11 is connected to an endoscope unit 24. The endoscope unit 24 is arranged in, for example, the control unit 12 shown in FIG. 1. Further, the endoscope unit 24 comprises a light source device (not shown) for obtaining illumination light necessary for photographing and an electric bending device (not shown) for electrically bending the endoscope insertion portion 11 freely.

An image pick-up signal from a solid image pick-up device 43 (refer to FIG. 5) at the tip of the endoscope insertion portion 11 is inputted to a camera control unit (hereinafter, referred to as a CCU) 25. The CCU 25 converts the supplied image pick-up signal into a video signal such as an NTSC signal, and supplies the converted signal to main processing circuits in the control unit 12.

Referring to FIG. 2, the main circuits provided in the control unit 12 include a CPU 26 for controlling the execution and operation of various functions based on a main program, a ROM 27, a RAM 28, a PC card interface (hereinafter, referred to as a PC card I/F) 30, a USB interface (hereinafter, referred to as a USB I/F) 31, an RS-232C interface (hereinafter, referred to as an RS-232C I/F) 29, an audio signal processing circuit 32, and a video signal processing circuit 33.

The RS-232C I/F 29 is connected respectively to the CCU 25, the endoscope unit 24, and the remote controller 13. The remote controller 13 controls and instructs the operation of the CCU 25 and the endoscope unit 24. The RS-232C I/F 29 performs the communication necessary for controlling the operation of the CCU 25 and the endoscope unit 24 based on the operation of the remote controller 13.

The USB I/F 31 is an interface for electrically connecting the control unit 12 and a personal computer 21. When the control unit 12 and the personal computer 21 are connected via the USB I/F 31, various control operations by instructions such as that for displaying the endoscope image and that for image-processing upon measuring by the control unit 12 can be implemented via the personal computer 21. Further, control information and data necessary for various processing can be received and transmitted between the control unit 12 and the personal computer 21.

A PCMCIA memory card 22 and a compact flash (R) memory card 23 can detachably be connected to the PC card I/F 30. That is, when any memory card is attached, the control unit 12 can reproduce data on control processing information or image information which is stored in the memory card as a recording medium and fetch the reproduced data in the control unit 12 via the PC card I/F 30, or can supply the data on the image information or on the control processing information to the memory card via the PC card I/F 30 and record the data, under the control of the CPU 26.

The video signal processing circuit 33 combines a video signal from the CCU 25 and a display signal based on an operation menu which is generated under the control of the CPU 26 so as to display a combined image obtained by combining the endoscope image supplied from the CCU 25 and the graphically displayed operation menu. Further, the video signal processing circuit 33 supplies a video signal subjected to processing necessary for displaying the data to the LCD 14 therein. Thus, the combined image of the endoscope image and the operation menu is displayed on the LCD 14. Incidentally, the video signal processing circuit 33 can perform processing for displaying singly the endoscope image or the operation menu image.

An external video input terminal 70 for inputting a video signal to the video signal processing circuit 33 not via the CCU 25 is independently provided for the control unit 12 shown in FIG. 1. When the video signal is inputted to the external video input terminal 70, the video signal processing circuit 33 outputs the combined image, prior to the endoscope image from the CCU 25.

An audio signal which is collected and generated by a microphone 20 and is recorded to the recording medium such as a memory card, an audio signal which is obtained by reading a signal on the recording medium such as a memory card, or an audio signal generated by the CPU 26 is supplied to the audio signal processing circuit 32. The audio signal processing circuit 32 subjects the supplied audio signal to processing necessary for reproducing the supplied signal (amplification), and outputs the audio signal to a speaker 19. As a consequence, the audio signal is reproduced by the speaker 19.

The CPU 26 executes a program stored in the ROM 27, and performs the control operation of the entire system by various circuit units so as to execute processing corresponding to each purpose.

The remote controller 13 comprises a joy stick 47, a lever switch 48, a freeze switch 49, a store switch 50, and a measuring execution switch 51, as shown in FIG. 7, which are provided together for at least an upper surface of a casing.

In the remote controller 13, the joy stick 47 is a switch for performing bending operation of the tip of the endoscope, and can freely instruct the operation in any direction with an angle of 360°. The lever switch 48 is a switch for moving a pointer when performing various menu operation graphically displayed or performing the measurement, and is formed with an almost similar shape of the joy stick 47. The freeze switch 49 is a switch which is used when displaying a moving picture of the endoscope displayed on the LCD 14 as a still image. The store switch 50 is a switch which is used when recording the still image to the PCMCIA memory card 22 (refer to FIG. 2), in the case of displaying the still image by pressing the freeze switch 49. The measuring execution switch 51 is a switch which is used when software for measuring is executed.

Incidentally, the freeze switch 49, the store switch 50, and the measuring execution switch 51 are on/off type pressing switches.

Next, a description is given of the structure of the stereo optical adaptor as one type of optical adaptors used for the measuring endoscope apparatus 10 according to the first embodiment with reference to FIGS. 4 to 6.

Referring to FIGS. 4 and 5, a stereo optical adaptor 37 is attached to the tip of the endoscope 39. The stereo optical adaptor 37 is fixed by being spiraled to an external screw 54 of the tip of the endoscope 39 by using an internal screw 53 of a fixing ring 38.

A pair of illumination lenses 36 and two objective lens systems 34 and 35 are mounted on the tip of the stereo optical adaptor 37. The two objective lenses 34 and 35 form two images on the image pick-up device 43 arranged in the tip 39 of the endoscope. An image pick-up signal obtained by the image pick-up device 43 is supplied to the CCU 25 via an electrically connected signal line 43a and the endoscope unit 24 shown in FIG. 2. The CCU 25 converts the supplied signal into a video signal and thereafter supplies the resultant signal to the video signal processing circuit 33. Thus, for example, an image 14a as shown in FIG. 6 is displayed on the screen of the LCD 14.

The measuring endoscope apparatus 10 with the above-mentioned structure comprises an image pick-up unit for observation (image pick-up device 43) and a plurality of observation optical systems for forming an image of an observation target on the image pick-up unit as observed images from a plurality of view points (objective lens systems 34 and 35) at the tip of the long endoscope insertion portion 11.

Further, the measuring endoscope apparatus 10 comprises: a processing unit (CCU 25, CPU 26, ROM 27, RAM 28, and video signal processing circuit 33) for receiving a signal from the image pick-up unit (image pick-up device 43), performing the processing of the received signal, and generating the video signal; and a display device for receiving the video signal from the processing unit and displaying the observed image (the LCD 14).

FIG. 3 shows the structure of a processing unit 62 which is realized by the CPU 26 or the like.

The processing unit 62 comprises an estimating unit 63 which estimates three-dimensional coordinates at an arbitrary point on the observation image based on image signals at view points that are obtained by the image pick-up unit and obtains the estimation result and the reliability thereof. The remote controller 13 comprises a cut-off datum line input unit 61 for inputting a cut-off datum line as a datum for setting a position of a cut-off plane of the observation target.

The processing unit 62 comprises a cross-section information generating unit 65, a concave and convex datum line setting unit 64, a concave and convex information generating unit 66, and a concave and convex information processing unit 67. The cross-section information generating unit 65 generates cross-section information of the observation target at the cut-off plane based on the estimation result of the estimating unit 63.

The concave and convex datum line setting unit 64 estimates the reliability at the point on the cut-off datum line based on the reliability of the estimation result of the estimating unit 63, and sets both new ends by extracting only a point which is determined to have high reliability. The concave and convex datum line setting unit 64 sets a concave and convex datum line as a predetermined datum for processing the cross-section information to create the concave and convex information indicating a relative concave and convex portion with respect to the predetermined cross-section information, based on both the set new ends.

The concave and convex information generating unit 66 generates the concave and convex information based on the cross-section information and the concave and convex datum line. The concave and convex information processing unit 67 processes the concave and convex information to create a concave and convex index by which the concave and convex information is visualized. The LCD 14 comprises a concave and convex index display unit 68 for displaying the concave and convex index.

Next, the operation according to the first embodiment will be described.

According to the first embodiment, the measuring endoscope apparatus 10 executes the stereo measurement of a subject as a measuring target based on optical data captured from the recording medium {such as the compact flash (R) memory card} on which the optical data from the stereo optical adaptor 37 is recorded, by using the endoscope image shown in FIG. 6.

The stereo measurement by the measuring endoscope apparatus 10 is performed by executing at least: first processing for reading optical information from the recording medium {such as the compact flash (R) memory card} on which the optical data from the stereo optical adaptor 37 is recorded; second processing for reading the position information between the image pick-up device 43 in the tip of the endoscope 39 and the objective lens systems 34 and 35 in the stereo optical adaptor 37; third processing for obtaining a position error of the image pick-up device 43 based on the read information on the positional relationship and main information on the positional relationship between the image pick-up device 43 in the endoscope and the objective lens systems 34 and 35 in the stereo optical adaptor 37 obtained upon manufacturing; fourth processing for correcting the optical data based on the position error; fifth processing for generating two corrected images (corrected datum image and corrected reference image) which are obtained by coordinate-transforming a half image on the left (datum image) and a half image on the right (reference image) that are subjected to the measurement based on the corrected optical data; and sixth processing for obtaining three-dimensional coordinates at an arbitrary point by matching the two images based on the corrected images.

The CPU 26 subjects the stereo optical adaptor 37 to, for example, the first to fourth processing once, and controls the operation so that the processing results are recorded to the compact flash (R) memory card 23 as data on the measuring environment. The first to fourth processing is called calibration. Upon executing the stereo measurement after that, the CPU 26 controls the operation for loading the data on the measuring environment to the RAM and then executing the fifth and sixth processing.

The second processing for reading the information on the positional relationship between the image pick-up device 43 at the tip of the endoscope 39 and the objective lens systems 34 and 35 in the stereo optical adaptor 37 is performed by capturing the shape of a mask provided for the stereo optical adaptor 37 and comparing the mask shape and mask position upon manufacturing. In this case, the mask shape is obtained by capturing a white image (e.g., reflecting a white sheet). The brightness of the white image in this case is determined depending on the gain of the CCU 25 and the shutter speed.

Ordinarily, the gain of the CCU 25 and the shutter speed of the image pick-up device 43 are automatically controlled so as to match the best condition. However, when automatically controlling the gain of the CCU 25 and the shutter speed, the gain of the CCU 25 is set to be low and the shutter speed of the image pick-up device 43 is set to be high and therefore the image is dark and the mask shape cannot clearly be photographed. This gives an adverse influence to the measuring accuracy. Thus, according to the first embodiment, the gain of the CCU 25 and the shutter speed are fixed under the control of the CPU 26. Accordingly, the mask shape can be captured without fail and the decrease in measuring precision is prevented. The data on the measuring environment contains two types of tables, that is, an optical data table including the corrected optical data and the information on the positional relationship between the image pick-up device 43 and the objective lenses 34 and 35 of the stereo optical adaptor 37 and a coordinate transformation table for correcting the subject image. Under the control of the CPU 26, the data on the environment is recorded to the detachable compact flash (R) memory card 23.

Further, according to the first embodiment, the image is recorded to the PCMCIA memory card 22 under the control of the CPU 26. That is, under the control of the CPU 26, the image is recorded to a memory card different from the compact flash memory (R) card 23 for recording the data on the measuring environment.

For example, when an observer performs the measurement of the length of a crack 44 indicated in the endoscope image in FIG. 6 by operating the remote controller 13, the observer presses the measuring execution switch 51 during observation, thereby shifting the screen to that for executing the stereo measurement. By selecting a measurement mode switching icon 83 (refer to FIG. 9) arranged on the screen in the above-mentioned state, the state shifts to a mode for measurement of the entire length, the observer designates a measuring point by a polyline to trace the crack 44 on the left of the screen (datum image). The CPU 26 searches for a corresponding point on the right of the screen (reference image) upon every designation of a new measuring point, obtains three-dimensional coordinates at the measuring point based on coordinates of the measuring point and the corresponding point, calculates a distance between two points, a point finally designated based on the three-dimensional coordinates and a point one-previously designated, calculates the sum of the distances, and displays the entire length of the crack 44 on the LCD 14.

When finding, for example, a concave portion 80a as shown in FIG. 8 during observing the monitor, the concave portion 80a is subjected to the measurement of the concave and convex portion. By pressing the measuring execution switch 51, the screen on the LCD 14 shifts to a screen for executing the stereo measurement execution screen 14a shown in FIG. 9. Thereafter, by selecting the measurement mode switching icon 83 arranged on the screen, the state shifts to a cross-section measurement mode.

An icon for measuring operation is displayed by being overlapped on the observation image, as shown in FIG. 9. Thus, advantageously, a time before the start of measuring can be reduced because the apparatus enters a state in which the start of measuring is possible, only by performing the fifth processing (coordinate transformation of the measuring image), and thus processing for displaying the icon for operation, and processing for cutting off the image for display performed upon the conventional stereo measurement can be omitted.

A datum image 81 and a reference image 82 are displayed on the screen for executing the stereo measuring execution screen 14a. Further, on the screen for executing the stereo measurement execution screen 14a, a measurement mode switching icon 83, a menu icon 84, a clear icon 85, an end icon 86, and a number display area 87 are overlappingly displayed.

The measurement mode is changed by selecting the measurement mode switching icon 83. The measurement mode switching icon 83 simultaneously has a function for displaying the current measurement mode and can be switched by a toggle.

A menu for the stereo measurement (not shown) is displayed by selecting the menu icon 84.

When the clear icon 85 is selected, all graphics such as a point or a line which is inputted for the purpose of executing the measurement are erased and, thus, the measurement can be performed again from the starting point.

The stereo measurement is ended by selecting the end icon 86.

Points A and B as two datum points for determining the cut-off datum line for specifying the cut-off plane position of a portion whose cross-section information for measuring is to be obtained are designated on the datum image 81 in FIG. 9 as shown by step S101 in FIG. 13 via the cut-off datum line input unit 61. The observer performs the operation by using the lever switch 48 and moving the pointer 88 displayed on the screen 14a.

The cut-off plane determined by the operation will be described with reference to FIG. 10. Points A1 and B1 corresponding to the points A and B are determined on a correction datum image 89 in FIG. 10 by designating the points A and B on the datum image 81 in FIG. 9 by the observer. A line connecting the points A1 and B1 becomes a cut-off datum line (hereinafter, abbreviated to a datum line) 90. Originally, an image of an observation target 80 is formed as an inverted image opposite to the observation target sandwiching an optical center. However, for the purpose of understandability, the correction datum image 89 generated by coordinate-transforming the datum image 81 by the fifth processing is placed as an erect image between the observation target 80 and an optical center L of the objective optical system for the datum image.

A cut-off plane 91 as a target of the observer is defined as a plane including the datum line 90 and the optical center L of the optical system by which the datum image is picked up.

Points A2 and B2 become mapping points on the surface of the observation target 80 of the points A1 and B1 on the correction datum image 89. That is, according to the first embodiment, a cross-section outer line 92 as a display target is defined as a common line between the cut-off plane 91 and the surface of the observation target 80 on the view point.

An optical axis 93 of the optical system for datum image vertically intersects to the correction datum image 89, and an intersection thereof is a point 0 on the correction datum image 89. Incidentally, reference numeral 93 denotes an optical axis shown by a broken line connecting the point 0 and the optical center L in FIG. 10.

As shown in step S102 in FIG. 13, the CPU 26 determines whether or not texture exists around each of all pixels on the datum line 90 on the correction datum image 89 as the correction image for measuring to obtain the cross-section information of the cut-off plane 91, and sets the pixel which is determined to have the texture as the target point. Since the reliability of the corresponding point tends to be deteriorated when the texture does not exist around the target point, it is possible to omit the operation for searching the corresponding point of the target point at which the reliability of the corresponding point is expected in advance to be deteriorated by the processing, and thus, it is possible to reduce a processing time.

In step S103, the CPU 26 searches for the corresponding point as the pixel on the correction reference image (not shown) corresponding to the target point by using corresponding point search means, and draws a corresponding-point group 103 as shown in FIG. 11.

In this case, all the corresponding points are searched on the corrected image. In the case of searching for the corresponding point, the corresponding point is searched by using an algorism for searching the corresponding point using information on all points around the target point, a so-called template matching (or window matching or block matching).

The corresponding points are drawn corresponding to the target points on the datum line 90 of the correction datum image 89 as shown in FIG. 10 by searching for the corresponding points. The corresponding-point group 103 as a group of the corresponding points on the screen for executing the stereo measuring execution screen 14a as shown in FIG. 11 is displayed on the reference image 82 by searching for the corresponding points of all the target points. In this case, the CPU 26 stores the degree of correspondence at the points.

When the corresponding point is not found upon searching for the corresponding point in step S103, the CPU 26 shifts the processing to step S104 whereupon the difference between the position of the target point on the correction datum image 89 and the position of the corresponding point on the correction reference image (not shown), that is, a parallax is obtained for every target point. Then, the CPU 26 shifts to the processing to step S105. In step S105, the CPU 26 calculates three-dimensional coordinates and three-dimensional coordinates on space on which the target point is mapped by the reliability estimating unit 63 based on the obtained parallax and optical data, such as a length of a basic line as a distance between the optical centers, obtained in advance, of the optical systems, a focusing distance of the optical systems, and coordinates of a mapping point to the corrected image for measuring the optical axis in the optical system.

After obtaining the three-coordinates of the corresponding points of all the target points set on the datum line 90 in step S105, the CPU 26 shifts the processing to step S106 whereupon it removes a point having a low degree of correspondence obtained in step S103 and a point whose three-dimensional coordinates are extremely apart from a near point thereof, from the original target point group and sets the cross-section information on the cut-off plane 91 as three-dimensional coordinates of the target point group based on the three-dimensional coordinates upon searching for the corresponding points.

Next, the CPU 26 shifts the processing to step S107 whereupon a concave and convex datum line (a concave and convex datum line 90a shown in FIG. 11) is set.

Content in step S107 will be described in detail with reference to FIG. 14.

In step S201, the CPU 26 first starts to sequentially search in a direction to the point B1 starting from the point A1. In step S202, the CPU 206 shifts the processing to the next point. In step 203, the CPU 26 obtains a distance of the three-dimensional coordinates between the current point and one-previous point.

In step S204, the CPU 26 determines whether or not the distance obtained in step S203 is equal to a predetermined value or more. If TRUE in step S204, the CPU returns to step S202.

If NOT TRUE in the determination in step S204, the CPU 26 sets a one-previous point as a start point of the concave and convex datum line 90a and shifts the processing to step S206. In steps S206 to S210, the CPU 26 performs the same processing in steps S201 to S205 in the reverse direction, and sets an end point of the concave and convex datum line 90a. In the processing in steps S201 to S210, the CPU 26 sets the concave and convex datum line 90a and shifts the processing to step S108.

In step S108, the CPU 26 obtains a distance from the concave and convex datum line 90a at each point of the cross-section information on space. In step S109, the CPU 26 expresses the obtained distance in the vertical direction to a segment AB on the datum image 81. Thus, the CPU 26 displays on the LCD 14, the cross-section outer line 92 overlapped on the datum image 81 in FIG. 10 as a concave and convex index 94 shown in FIG. 11. Thus, the position on the datum image 81 can be easily corresponded to a concave and convex state of the position.

However, upon displaying the data on the LCD 14, a depth direction is changed depending on the position of the segment AB (or the concave and convex datum line 90a) on the datum image 81 and on whether the point of the information on the cross section, having a maximum distance from the concave and convex datum line 90a, is located on the back side or on the front side. More specifically, as shown in FIG. 11, when the segment AB exists on the right side of the center of the datum image 81 and the point having the maximum distance from the concave and convex line 90a exists on the back side, the concave and convex index 94 is formed so that the left direction on the screen corresponds to the back side. On the other hand, as shown in FIG. 12, when the segment AB as the observation target is located on the left side of the center of the datum image 81, the concave and convex index 94 is formed so that the left direction on the screen is on the back side. FIG. 11 shows an example in which the segment AB is in the longitudinal direction on the datum image 81. In a state in which the segment AB is in the lateral direction on the datum image 81, the section AB can almost similarly be expressed. For example, as shown by the datum image 81 in FIG. 17, which will be described later, the concave and convex index 94 can be formed. Thus, advantageously, the possibility that a part of the concave and convex index 94 exists out of the screen is reduced.

Similarly to the above-mentioned display, the measuring endoscope apparatus 10 displays a distance between a point determined as the start point by the CPU 26 and a point determined as the end point on a number display area 87. Accordingly, the dimension of the observation target can easily be estimated.

As described above, the measuring endoscope apparatus 10 shifts to the stereo measurement mode while the observer observes the target, and the observer designates two points on the datum image 81 displayed on the monitor screen. Thereby, it is possible to form the cut-off datum line so that a portion to be observed by the observer is easily positioned.

The measuring endoscope apparatus 10 causes the LCD 14 to display the cross-section information of the cut-off datum line designated by the observer as the concave and convex index desired by the observer. Thereby, the observer can examine the subject for a short time by easily grasping the cross-section shape.

The first embodiment has the following advantages.

As mentioned above, according to the first embodiment, it is possible to provide the measuring endoscope apparatus which can accurately grasp the shape of the observation target by setting the concave and convex datum line 90a based on the point whose coordinates can be estimated more accurately than the point set by the user upon designating the cut-off datum line 90, and by generating the concave and convex information of the observation target on the cut-off plane whose measurement is desired. Advantageously, since the concave and convex datum line 90a is automatically set, the user can easily designate the cut-off plane of the shape of the observation target without paying attention to the presence or absence of the texture of the image upon designating the cut-off datum line 90. In addition, advantageously, it is possible to suppress the possibility that a part of the concave and convex index 94 exists out of the screen by switching the direction of the concave and convex index 94 to the concave and convex datum line 90a so that the maximum point of the concave and convex index 94 exists the center side of the datum image.

Although not shown, a portion at which an interval between the points forming the cross-section outer line 92 is larger than a predetermined width, namely, a portion at which it is determined that the reliability of the cross-section outer line 92 is low, can be displayed by a broken line and other portions can be displayed by a solid line. Consequently, advantageously, it is possible to suppress the possibility that the user erroneously recognizes the shape of the observation target. The similar advantage is obtained not by changing the type of line depending on the reliability but by changing a line color.

According to the first embodiment, when determining points at both ends of the concave and convex datum line 90a, the points are searched only in a direction for reducing the length of the concave and convex datum line 90a. However, when the points are searched simultaneously in a direction for extending the concave and convex datum line 90a, the similar advantage is obtained. In this case, the concave and convex datum line setting unit 64 estimates the reliability of the point on the cut-off datum line 90 and the point on the extending line, extracts only the point whose reliability is high and sets both new ends, and sets the concave and convex datum line 90a as a predetermined datum from both the new ends.

(Second Embodiment)

Figure 15:
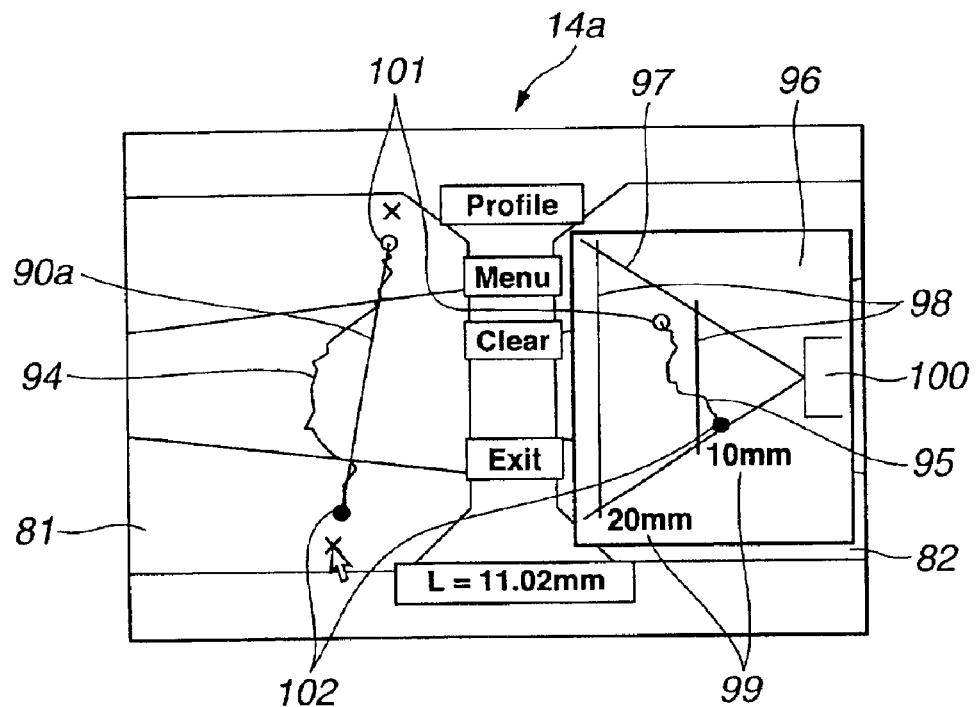
FIG. 15 is an explanatory diagram showing a first example of a screen for displaying contour index by a measuring endoscope apparatus according to a second embodiment of the present invention.
Figure 16:
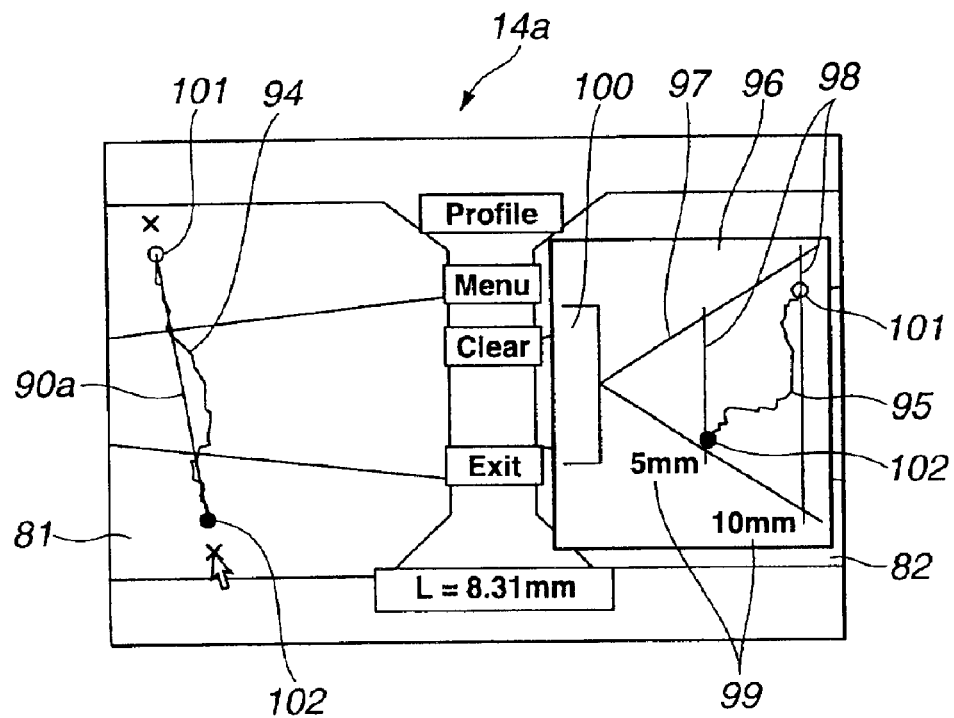
FIG. 16 is an explanatory diagram showing a second example of the screen for displaying the contour index by the measuring endoscope apparatus according to the second embodiment of the present invention.
Figure 17:
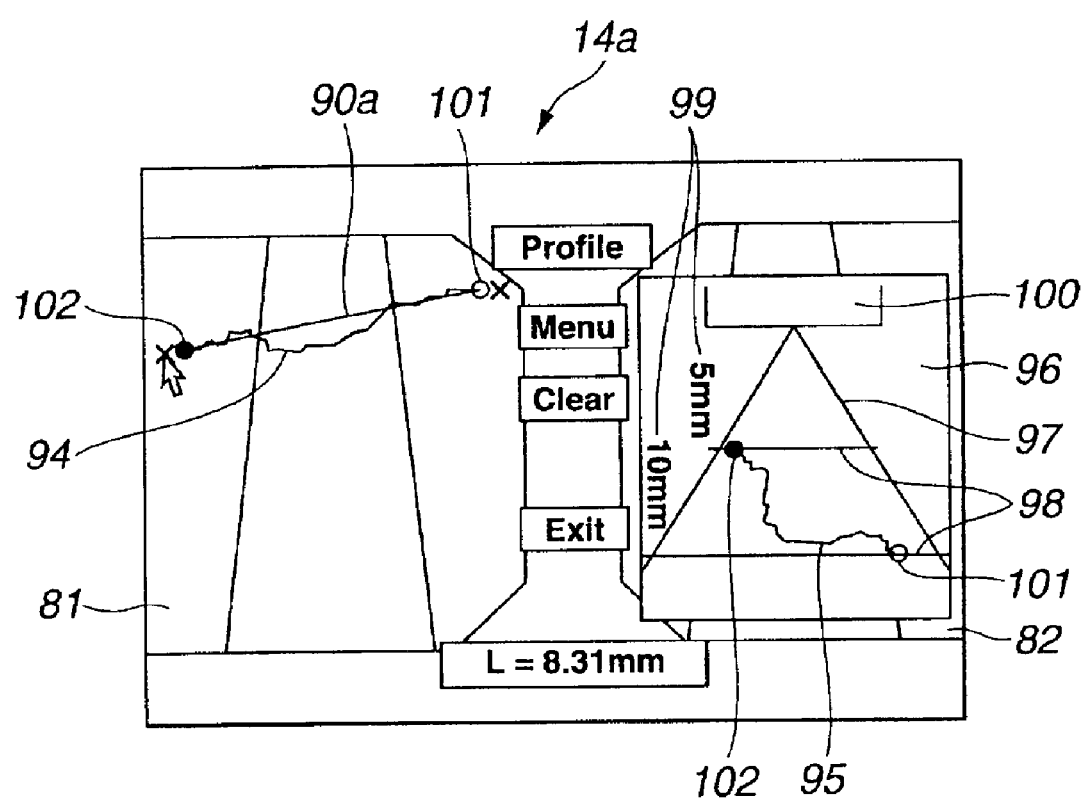
FIG. 17 is an explanatory diagram showing a third example of the screen for displaying the contour index by the measuring endoscope apparatus according to the second embodiment of the present invention.
Figure 18:
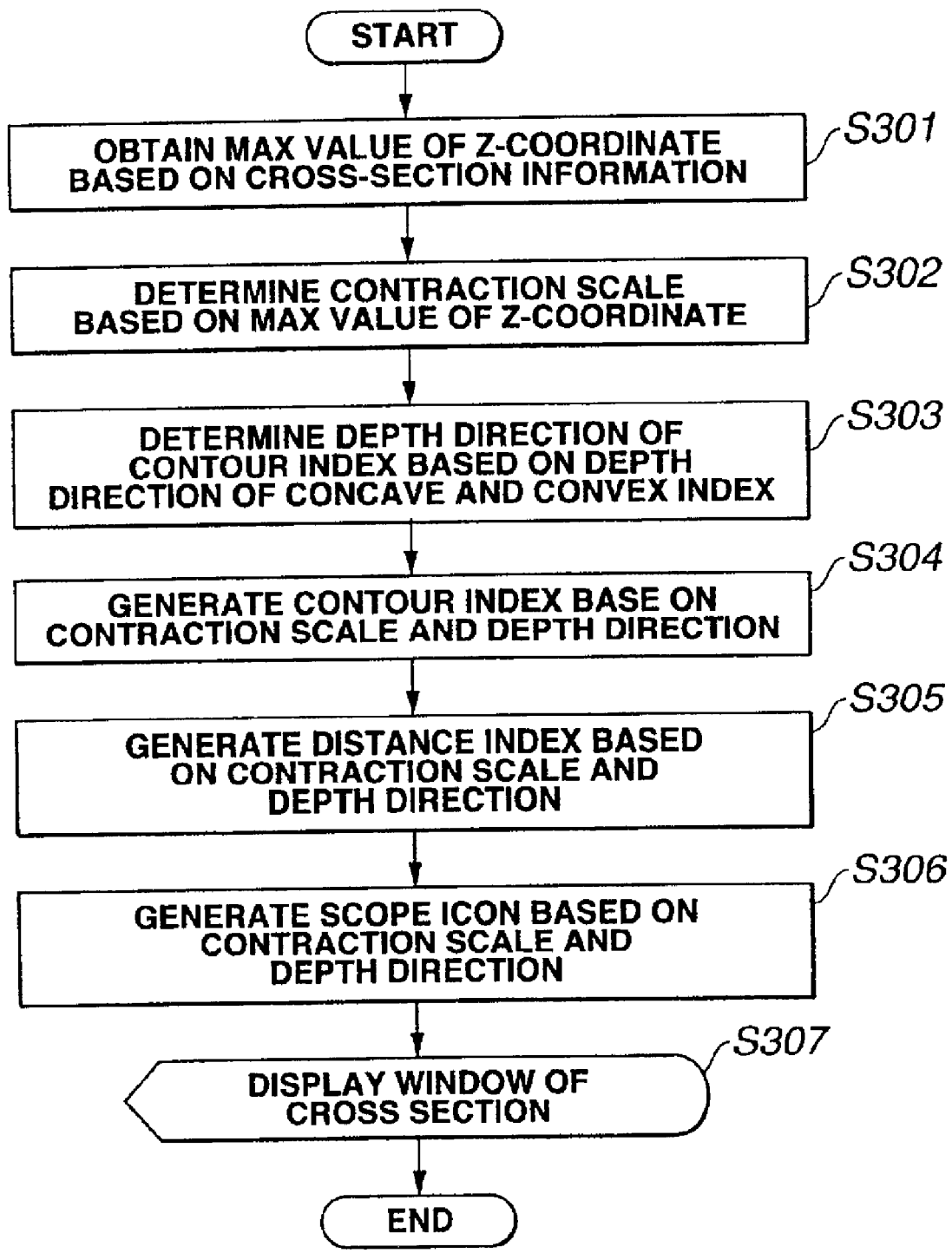
FIG. 18 is a flowchart showing the processing for displaying a window of a cross section by the measuring endoscope apparatus according to the second embodiment of the present invention.
Figure 19:
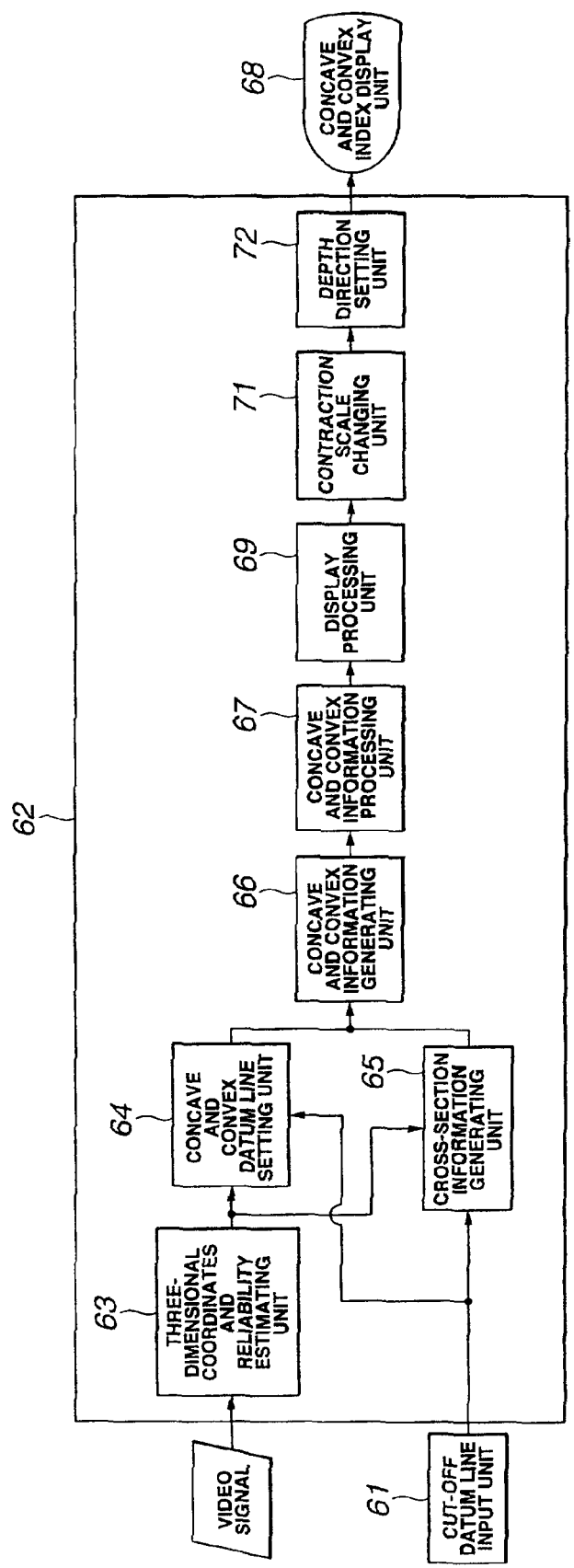
FIG. 19 is a functional diagram showing processing of a CPU in the measuring endoscope apparatus according to the second embodiment of the present invention.

FIGS. 15 to 18 relate to a second embodiment of the present invention, FIG. 15 is an explanatory diagram showing a first example of the screen for displaying the contour index, FIG. 16 is an explanatory diagram showing a second example of the screen for displaying the contour index, FIG. 17 is an explanatory diagram showing a third example of the screen for displaying the contour index, and FIG. 18 is a flowchart showing processing for displaying the window of the cross section. FIG. 19 is a functional block diagram showing processing by a CPU in a measuring endoscope apparatus according to the second embodiment of the present invention. According to the second embodiment, components are described by using those in FIGS. 1 to 7.

According to the second embodiment, a program stored in the ROM 27 is unlike the first embodiment, and other components are the same as those in the first embodiments.

According to the second embodiment, a processing unit 62 (CCU 25, CPU 26, ROM 27, RAM 28, and video signal processing circuit 33) changes the program stored in the ROM 27, thereby having a display processing unit 69 (refer to FIG. 19) for displaying a contour index 95 as a measured result of the cross section as shown in FIG. 15, additionally to the components of the first embodiment. The observation index 95 is displayed on a cross-section result window 96 drawn on the reference image 82. In this case, the cross-section result window 96 displays a field-of-view index 97 indicating a filed of view of the endoscope, a distance index 98 indicating a distance from the tip of the endoscope, a substance distance 99 indicating a distance from the tip of the endoscope of the distance index, and a scope icon 100 indicating the tip of the endoscope. The contour index 95, the distance index 98, and the scope icon 100 are displayed with the same contraction scale.

Further, according to the second embodiment, a contraction scale change unit 71 for changing the contraction scale of the contour index 95, the distance index 98, and the scope icon 100, by using a maximum value of a z-coordinate of the cross-section information is provided. Advantageously, on the above-mentioned display operation, it is possible to prevent the size of the cross-section outer line diagram based on the concave and convex index 94 from being reduced and becoming uneasy to view, and to clearly grasp the distance from the tip of the endoscope of the observation target and the size of the observation target.

FIG. 16 is an example in which a position different from that in FIG. 15 is subjected to the measurement and the result is displayed with another contraction scale.

Further, referring to FIG. 17, according to the second embodiment, a depth direction setting unit 72 is provided for switching the cross-section result window 96 to four directions by the depth direction of the concave and convex index 94 and an inclination of the concave and convex datum line 90a in the depth direction on the datum image 81. A start cursor 101 and an end cursor 102 are drawn also at a start point and an end point of the concave and convex index 94, respectively. The start cursor 101 and the end cursor 102 are similarly drawn at positions corresponding to the contour index 95. Thus, advantageously, the concave and convex index 94 can easily correspond to the contour index 95.

Other structure is substantially the same as that of the first embodiment.

Next, the operation according to the second embodiment will be described.

The operation to display the cross section window will be described with reference to FIG. 18. Processing in FIG. 18 is executed after ending processing in step S109 in FIG. 13 according to the first embodiment.

In step S301, the CPU 26 obtains a value z_max as a maximum value of the z-coordinate based on the cross-section information.

In processing in step S302, the CPU 26 determines the contraction scale upon displaying the contour index 95, the distance index 98, and the scope icon 100 on the cross-section result window 96. In this processing, the value z_max is divided into three cases of, for example, a case in which it is less than 10 mm, a case in which it is not less than 10 mm and less than 20 mm, and a case in which it is not less than 20 mm and less than 40 mm. For instance, the contraction scale is set so that the range up to z_max can be drawn within a range of 70% of the width and the height of the cross-section result window 96. In the case in which the value z_max is not less than 40 mm, the same contraction scale in the case in which the value z_max is not less than 20 mm and less than 40 mm is applied.

In step S303, the CPU 26 sets the depth direction of the contour index 95 based on the depth direction of the concave and convex index 94. In this case, the CPU 26 sets an angle in the counterclockwise direction when a right direction of the horizontal direction on the screen of the LCD 14 is set to 0°. When the depth direction of the concave and convex index 94 is not less than −45° and less than 45°, the CPU 26 sets the depth direction of the contour index 95 to the right direction. When the depth direction of the concave and convex index 94 is not less than 45° and is less than 135°, the CPU 26 sets the depth direction of the contour index 95 to the upper direction. When the depth direction of the concave and convex index 94 is not less than 135° and is less than 225°, the CPU 26 sets the depth direction of the contour index 95 to the lower direction.

Next, the CPU 26 generates the contour index 95 in step S304. In this case, the CPU 26 first generates two-dimensional coordinates obtained by projecting the three-dimensional coordinates of the cross-section information on the cut-off plane. Thereafter, the CPU 26 transforms the coordinates in accordance with the above-obtained contraction scale and the depth direction, and draws the observation target onto the cross-section result window 96 as the contour index 95.

In steps S305 and S306, the CPU 26 similarly generates the distance index 98 and the scope icon 100. In step S307, the CPU 26 displays the cross-section result window 96.

Other operation is substantially the same as that of the first embodiment.

The second embodiment has the following advantages.

As mentioned above, according to the second embodiment, the same advantages as those shown in FIGS. 1 to 14 according to the first embodiment are obtained. By displaying the concave and convex index 94 and the contour index 95 as well, which is more approximate to the actual shape of the observation target, and by changing the depth direction of the contour index 95 to match the depth direction of the concave and convex index 94, the correspondence between the concave and convex index 94 and the contour index 95 can easily be recognized. That is, advantageously, the shape of the observation target can easily be grasped.

According to the first and second embodiments shown in FIGS. 1 to 18, the present invention is applied to the measuring endoscope apparatus. However, the present invention may be applied to an image-processing measuring apparatus other than the measuring endoscope apparatus, such as an image-processing measuring apparatus for measuring an outer shape of a solid subject.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An image-processing measuring apparatus comprising:
   one or a plurality of image pick-up units for observation;
   one or a plurality of observation optical systems for forming an observation target on said image pick-up unit as an observed image from one or a plurality of view points;
   a processing unit for receiving a signal from said image pick-up unit, performing processing of the received signal, and generating a video signal;
   a display device for receiving and displaying the video signal from said processing unit and displaying said observation image;
   an estimating unit for estimating three-dimensional coordinates at an arbitrary point on said observed image based on an image signal in each view point obtained by said image pick-up unit, and for obtaining the estimation result and the reliability of the estimation result;
   a cut-off datum line input unit for inputting a cut-off datum line as a datum for setting a position of a cut-off plane of said observation target;
   a cross-section information generating unit for generating cross-section information of said observation target on said cut-off plane based on the estimation result of said estimating unit;
   a concave and convex datum line setting unit for estimating the reliability of a point on said cut-off datum line or on an extending line of said cut-off datum line based an the reliability of the estimation result of said estimating unit, extracting only a point whose reliability is high and setting both new ends, and setting a concave and convex datum line as a predetermined datum, based on both the set new ends;
   a concave and convex information generating unit for generating concave and convex information by treating said cross-section information to create said concave and convex information indicating a relative concave and convex state with respect to said concave and convex datum line;
   a concave and convex information processing unit for processing said concave and convex information to a visualized concave and convex index; and
   a concave and convex index display unit for displaying said concave and convex index.

2. A measuring endoscope apparatus comprising:

an endoscope insertion portion having at a tip thereof, one or a plurality of image pick-up units for observation and one or a plurality of observation optical systems for forming the image of an observation target on said image pick-up unit as an observed image in one or a plurality of view points;

a processing unit for receiving a signal from said image pick-up unit, performing processing of the received signal, and generating a video signal;

a display device for receiving and displaying the video signal from said processing unit and displaying said observed image;

an estimating unit for estimating three-dimensional coordinates at an arbitrary point an said observed image based on an image signal in each view point obtained by said image pick-up unit, and for obtaining the estimation result and the reliability of said estimation result;

a cut-off datum line input unit for inputting a cut-off datum line as a datum for setting a position of a cut-off plane of said observation target;

a crass-section information generating unit for generating cross-section information of said observed target on said cut-off plane based on the estimation result of said estimating unit;

a concave and convex datum line setting unit for estimating the reliability of a point on said cut-off datum line or on an extending line of said cut-off datum line based on the reliability of the estimation result of said estimating unit, extracting only a point whose reliability is high and setting both new ends, and setting a concave and convex datum line as a predetermined datum based on both the new ends;

a concave and convex information generating unit for generating concave and convex information by processing said cross-section information to said concave and convex information indicating a relative concave and convex state with respect to said concave and convex datum line;

a concave and convex information processing unit for processing said concave and convex information to create a visualized concave and convex index; and a concave and convex index display unit for displaying said concave and convex index.

3. An image-processing measuring apparatus comprising:

one or a plurality of image pick-up units for observation;

one or a plurality of observation optical systems for forming an observation target on said image pick-up unit as an observation image from one or a plurality of view points;

a processing unit for receiving a signal from said image pick-up unit, performing processing of the received signal, and generating a video signal; and a display device for receiving and displaying the video signal from said processing unit and displaying said observed image, wherein said processing unit comprises an estimating unit for estimating three-dimensional coordinates at an arbitrary point on said observation image based on an image signal in each view point obtained by said image pick-up unit, and obtaining the estimation result and the reliability of said estimation result, said image-processing measuring apparatus farther comprising:

a cut-off datum line input unit for inputting a cut-off datum line as a datum for setting a position of a cut-off plane of said observation target;

a cross-section information generating unit for generating cross-section information of said observation target on said cut-off plane based on the estimation result of said estimating unit;

a concave and convex datum line setting unit for estimating the reliability of a point on said cut-off datum line or on an extending line of said cut-off datum line based on the reliability at the estimation result of said estimating unit, extracting only a point whose reliability is high and setting both new ends, and netting a concave and convex datum line as a predetermined datum indicating a relative concave and convex state with respect to said predetermined datum based on both the new ends;

a concave and convex information generating unit for generating said concave and convex information based on said cross-section information and said concave and convex datum line;

a concave and convex information processing unit for processing said concave and convex information to create a concave and convex index by which said concave and convex information is visualized; and a concave and convex index display unit for displaying said concave and convex index.

4. The image-processing measuring apparatus according to claim 3, wherein said concave and convex datum line setting unit comprises:

an extracting unit for extracting two points on said cut-off datum line; and a concave and convex datum line generating unit for generating a concave and convex datum line as a line for connecting said two points.

5. The image-processing measuring apparatus according to claim 4, further comprising a combining and display unit for overlapping said concave and convex index on said observation target image and displaying the overlapped image.

6. The image-processing measuring apparatus according to claim 5, wherein said display device comprises said concave and convex index display unit.

7. The image-processing measuring apparatus according to claim 3, further comprising a combining and display unit far overlapping said concave and convex index on said observation target image.

8. The image-processing measuring apparatus according to claim 3, wherein said display device comprises said concave and convex index display unit.

9. The image-processing measuring apparatus according to claim 8, further comprising a combining and display unit for overlapping said concave and convex index on said observation target image and displaying the overlapped image.

10. The image-processing measuring apparatus according to claim 3, further comprising:

a cross-section information processing unit for processing said cross-section information to create a contour index by which said cross-section information is visualized in a format for projecting it on a predetermined plane on apace; and a contour index display unit for displaying said contour index.

11. The image-processing measuring apparatus according to claim 10, further comprising
an adjusting unit for adjusting a depth direction of said contour index in accordance with an inclination of said concave and convex datum line and the setting of a direction of said concave and convex index.

12. The image-processing measuring apparatus according to claim 11, wherein said predetermined plane is said cut-off plane which is set by said cut-off datum line.

13. The image-processing measuring apparatus according to claim 12, wherein said concave and convex datum line setting unit comprises:
an extracting unit for extracting two points on said cut-off datum line; and
a concave and convex datum line generating unit for generating a concave and convex datum line as a line for connecting said two points.

14. The image-processing measuring apparatus according to claim 13, wherein said display device comprises said contour index display unit.

15. The image-processing measuring apparatus according to claim 13, wherein said display device comprises said concave and convex index display unit.

16. The image-processing measuring apparatus according to claim 13, wherein said display device comprises said concave and convex index display unit and said contour index display unit.

17. A measuring endoscope apparatus comprising:
a long insertion portion having at a tip thereof, one or a plurality of image pick-up units for observation and one or a plurality of observation optical systems for forming an observation target an said image pick-up unit as an observed image in one or a plurality of view points;
a processing unit for receiving a signal from said image pick-up unit, performing processing of the received signal, and generating a video signal; and
a display device for receiving and displaying the video signal from said processing unit and displaying said observation image,
wherein said processing unit comprises an estimating unit for estimating three-dimensional coordinates at an arbitrary point on said observation image based on an image signal in each view point obtained by said image pick-up unit, and obtaining the estimation result and the reliability of said estimation result,
said measuring endoscope apparatus further comprising:
a cut-off datum line input unit for inputting a cut-off datum line as a datum for setting a position of a cut-off plane to get cross-section information of said observation target;
a cross-section information generating unit for generating said cross-section information of the observation target on said cut-off plane based on the estimation result of said estimating unit;
a concave and convex datum line setting unit for estimating the reliability of a point on said cut-off datum line or on an extending line of said cut-off datum line based on the reliability at the estimation result of said estimating unit, extracting only a point whose reliability is high and setting both new ends, and setting a concave and convex datum line as a predetermined datum for processing said cross-section information to create concave and convex information indicating a relative concave and convex state with respect to said predetermined datum based on both the new ends;

a concave and convex information generating unit for generating said concave and convex information based on said cross-section information and said concave and convex datum line;
a concave and convex information processing unit for processing said concave and convex information to create a concave and convex index by which said concave and convex information is visualized; and
a concave and convex index display unit for displaying said concave and convex index.

18. The measuring endoscope apparatus according to claim 17, wherein said concave and convex datum line setting unit comprises:
an extracting unit for extracting two points on said cut-off datum line; and
a concave and convex datum line generating unit for generating a concave and convex datum line as a line for connecting said two points.

19. The measuring endoscope apparatus according to claim 18, further comprising
a combining and display unit for overlapping said concave and convex index on said observation target image and displaying the overlapped image.

20. The measuring endoscope apparatus according to claim 19, wherein said display device comprises said concave and convex index display unit.

21. The measuring endoscope apparatus according to claim 17, further comprising:
a combining and display unit for overlapping said concave and convex index on said observation target image and displaying said overlapped image.

22. The measuring endoscope apparatus according to claim 17, wherein said display device comprises said concave and convex index display unit.

23. The measuring endoscope apparatus according to claim 22, further comprising
a combining and display unit for overlapping said concave and convex index on said observation target image and displaying the overlapped image.

24. The measuring endoscope apparatus according to claim 17, further comprising:
a cross-section information processing unit for processing said cross-section information to create a contour index by which said cross-section information is visualized in a format for projecting it on a predetermined plane on space; and
a contour index display unit for displaying said contour index.

25. The measuring endoscope apparatus according to claim 24, further comprising:
an adjusting unit for adjusting a depth direction of said contour index in accordance with an inclination of said concave and convex datum line and the setting of a direction of said concave and convex index.

26. The measuring endoscope apparatus according to claim 25, wherein said predetermined plane is said cut-off.

27. The measuring endoscope apparatus according to claim 26, wherein said concave and convex datum line setting unit comprises:
an extracting unit for extracting two points on said cut-off datum line; and
a concave and convex datum line generating unit for generating a concave and convex datum line as a line for connecting said two points.

28. The measuring endoscope apparatus according to claim 27, wherein said display device comprises said contour index display unit.

29. The measuring endoscope apparatus according to claim 27, wherein said display device comprises said concave and convex index display unit.

30. The measuring endoscope apparatus according to claim 27, wherein said display device comprises said concave and convex index display unit and said contour index display unit.

* * * * *